United States Patent
Söchting et al.

(10) Patent No.: US 11,339,693 B2
(45) Date of Patent: May 24, 2022

(54) APPARATUS, DEVICE AND COMPUTER IMPLEMENTED METHOD FOR DETERMINING REMAINING LIFE OF ENGINE OIL IN ENGINE

(71) Applicant: Wärtsilä Finland Oy, Vaasa (FI)

(72) Inventors: Sven Söchting, Vaasa (FI); Ilona Söchting, Vaasa (FI)

(73) Assignee: Wärtsilä Finland Oy, Vaasa (FI)

( * ) Notice: Subject to any disclaimer, the term of this patent is extended or adjusted under 35 U.S.C. 154(b) by 0 days.

(21) Appl. No.: 17/256,365

(22) PCT Filed: Jul. 11, 2018

(86) PCT No.: PCT/FI2018/050540
§ 371 (c)(1),
(2) Date: Dec. 28, 2020

(87) PCT Pub. No.: WO2020/012058
PCT Pub. Date: Jan. 16, 2020

(65) Prior Publication Data
US 2021/0270156 A1   Sep. 2, 2021

(51) Int. Cl.
*F01M 11/10* (2006.01)
*G01N 33/28* (2006.01)
*F16N 29/04* (2006.01)

(52) U.S. Cl.
CPC .............. *F01M 11/10* (2013.01); *F16N 29/04* (2013.01); *G01N 33/2888* (2013.01);
(Continued)

(58) Field of Classification Search
CPC .................................................. F16N 2250/42
See application file for complete search history.

(56) References Cited

U.S. PATENT DOCUMENTS

| | | | | |
|---|---|---|---|---|
| 4,733,556 A | * | 3/1988 | Meitzler | ............... B01D 27/08 340/631 |
| 5,750,887 A | | 5/1998 | Schricker | |

(Continued)

FOREIGN PATENT DOCUMENTS

| | | | | |
|---|---|---|---|---|
| EP | 1296026 A1 | * | 3/2003 | ............. F01M 11/10 |
| EP | 1296026 A1 | | 3/2003 | |
| WO | WO-2006061222 A3 | * | 8/2006 | ............. B01D 39/18 |

OTHER PUBLICATIONS

International Search Report, Application No. PCT/FI2018/050540, dated Apr. 17, 2019, 2 pages.

*Primary Examiner* — Kevin R Steckbauer
(74) *Attorney, Agent, or Firm* — Ziegler IP Law Group, LLC

(57) ABSTRACT

A computer implemented method system and apparatus for determining remaining life of engine oil in an engine includes generating reference engine profile data by determining reference engine parameters of a reference engine; determining reference engine oil lubrication data based on mechanical testing of an oil sample from the reference engine; generating a reference model by associating the reference engine profile data with the reference engine oil lubrication data; receiving the reference model at an engine apparatus; measuring engine parameters relating to operation conditions of an engine of the engine apparatus; and determining remaining life of engine oil in the engine of the engine apparatus using the reference model and the engine parameters.

20 Claims, 7 Drawing Sheets

(52) U.S. Cl.
CPC ............... *F01M 2011/148* (2013.01); *F01M 2011/1426* (2013.01); *F01M 2011/1433* (2013.01); *F01M 2011/1486* (2013.01); *F16N 2250/36* (2013.01); *F16N 2250/42* (2013.01)

(56) References Cited

U.S. PATENT DOCUMENTS

| | | | | |
|---|---|---|---|---|
| 5,969,601 | A | 10/1999 | Sato et al. | |
| 7,355,415 | B2 * | 4/2008 | Boyle | G01N 33/2888 324/707 |
| 7,370,514 | B2 * | 5/2008 | Halalay | G01N 33/2888 73/53.05 |
| 7,392,142 | B2 * | 6/2008 | Kaldor | G01N 33/2888 702/22 |
| 7,835,875 | B2 * | 11/2010 | Halalay | G01N 33/2888 702/50 |
| 8,082,776 | B2 * | 12/2011 | Halalay | G01N 33/2888 73/114.55 |
| 8,087,287 | B2 * | 1/2012 | Cummings | G01N 33/2876 436/60 |
| 8,527,127 | B2 * | 9/2013 | Jacques | F01M 11/10 180/65.21 |
| 8,756,026 | B2 * | 6/2014 | Flandrois | G01N 27/10 702/65 |
| 9,244,054 | B2 * | 1/2016 | Schneider | G16Z 99/00 |
| 9,304,119 | B2 * | 4/2016 | De Kraker | G01N 33/2888 |
| 9,664,627 | B2 * | 5/2017 | Horstmeyer | F16N 39/00 |
| 9,714,931 | B2 * | 7/2017 | Prabhu | G01N 33/30 |
| 10,254,270 | B2 * | 4/2019 | Potyrailo | G01N 33/2888 |
| 10,260,388 | B2 * | 4/2019 | Potyrailo | G01N 33/2888 |
| 10,466,152 | B2 * | 11/2019 | Gillette, II | G01N 11/00 |
| 10,557,776 | B2 * | 2/2020 | Young | G01N 33/2876 |
| 10,591,388 | B2 * | 3/2020 | Young | G01N 35/00871 |
| 10,605,702 | B2 * | 3/2020 | Young | G01N 21/65 |
| 10,732,190 | B2 * | 8/2020 | Jean | G01N 35/00623 |
| 10,743,153 | B2 * | 8/2020 | Salvatore | H04L 12/40006 |
| 10,809,164 | B2 * | 10/2020 | Young | G06N 5/003 |
| 10,920,606 | B2 * | 2/2021 | Jean | F01D 21/003 |
| 2003/0051696 | A1 * | 3/2003 | Berndorfer | F01M 11/10 123/196 R |
| 2006/0232267 | A1 * | 10/2006 | Halalay | G01N 33/2888 508/110 |
| 2007/0032964 | A1 * | 2/2007 | Kaldor | G01N 33/30 702/189 |
| 2007/0151806 | A1 * | 7/2007 | Boyle | G01N 33/2888 184/6.21 |
| 2009/0192728 | A1 * | 7/2009 | Wright | G01N 33/2888 702/182 |
| 2010/0116022 | A1 * | 5/2010 | Cummings | G01N 33/2876 73/61.41 |
| 2010/0250156 | A1 * | 9/2010 | Halalay | F01M 11/10 702/50 |
| 2010/0300188 | A1 * | 12/2010 | Halalay | G01N 33/2888 73/290 R |
| 2012/0046896 | A1 * | 2/2012 | Flandrois | G01N 27/10 702/65 |
| 2012/0209460 | A1 * | 8/2012 | Jacques | F01M 11/10 903/902 |
| 2013/0230926 | A1 * | 9/2013 | De Kraker | G01N 21/75 436/60 |
| 2014/0019068 | A1 * | 1/2014 | Schneider | G01N 33/2888 702/30 |
| 2014/0343786 | A1 | 11/2014 | Dvorak et al. | |
| 2016/0054291 | A1 * | 2/2016 | O'Donnell | G01N 25/00 702/22 |
| 2016/0061805 | A1 * | 3/2016 | Prabhu | G01N 33/30 73/114.55 |
| 2016/0223469 | A1 * | 8/2016 | Horstmeyer | G01N 21/94 |
| 2017/0081997 | A1 * | 3/2017 | Potyrailo | G01N 33/2888 |
| 2017/0102308 | A1 * | 4/2017 | Gillette, II | F01M 11/10 |
| 2017/0138922 | A1 * | 5/2017 | Potyrailo | G01M 13/021 |
| 2017/0159485 | A1 * | 6/2017 | Jean | G01M 15/14 |
| 2018/0299355 | A1 * | 10/2018 | Young | G06N 20/10 |
| 2018/0299375 | A1 * | 10/2018 | Young | G01N 15/0656 |
| 2019/0090106 | A1 * | 3/2019 | Salvatore | H04L 12/403 |
| 2019/0101473 | A1 * | 4/2019 | Young | G06F 17/141 |
| 2019/0226947 | A1 * | 7/2019 | Young | G06N 20/10 |
| 2019/0234971 | A1 * | 8/2019 | Jean | F02D 41/22 |
| 2020/0056971 | A1 * | 2/2020 | Gillette, II | F01M 11/10 |
| 2020/0102851 | A1 * | 4/2020 | Jean | G16C 20/20 |
| 2020/0232356 | A1 * | 7/2020 | Fauda | G01N 33/2888 |
| 2021/0270156 | A1 * | 9/2021 | Söchting | F16N 29/04 |

* cited by examiner

APPARATUS, DEVICE AND COMPUTER IMPLEMENTED METHOD FOR DETERMINING REMAINING LIFE OF ENGINE OIL IN ENGINE

TECHNICAL FIELD

The present application generally relates to an apparatus, a device, a method and software code for determining remaining life of engine oil in an engine.

BRIEF DESCRIPTION OF RELATED DEVELOPMENTS

This section illustrates useful background information without admission of any technique described herein representative of the state of the art.

Modern vehicles, such as marine vessels, face fuel efficiency requirements that are becoming increasingly more stringent. New legislation in the United States and European Union within the past few years has set fuel economy and emissions targets not readily achievable with prior known vehicle and lubricant technology.

To address these increasing standards, engine equipment manufacturers are demanding better fuel economy as a lubricant-related performance characteristic, while maintaining deposit control and oxidative stability requirements. One well known way to increase fuel economy is to decrease the viscosity of the lubricating oil. However, this approach is now reaching the limits of current equipment capabilities and specifications. At a given viscosity, it is well known that adding organic or organic metallic friction modifiers reduces the surface friction of the lubricating oil and allows for better fuel economy. However, these additives often bring with them detrimental effects such as increased deposit formation, seals impacts, or they out-compete the anti-wear components for limited surface sites, thereby not allowing the formation of an anti-wear film, causing increased wear.

Furthermore, requirements for engine performances constantly increase. Such engine performance parameters comprise, for example, Brake Mean Effective Pressure (BMEP) and maximum cylinder pressure. Therefore, there will be more stress on the lubricant affecting lubricant lifetime (and service life).

Lubrication of an internal combustion piston engine is typically arranged be feeding lubrication medium, typically oil, to parts of the engine requiring lubrication by pressurizing the lubrication oil and leading pressurized oil to the desired locations by means of lubrication channels arranged to the engine. While the engine is operated, the quality of the oil decreases due to e.g. contaminants originating from combustion process and also wearing of the components of the engine. Usually a closed circulation loop is used in which the same amount of lubrication oil is gathered to an oil sump of the engine after participating in lubrication and pumped again to the desired lubrication locations after proper treatment like filtering. Before the lubrication and possibly other properties of the oil are deteriorated too much the oil is changed.

There is also drive to reduce engine service demands that will also create the demand to maximise lubricant life time. The quality of lubrication oil has great impact on the service life and required maintenance intervals of the engine.

It is known from the prior art to provide an arrangement for taking a sample of lubrication oil in an internal combustion engine from its cylinder's inner surface, in which arrangement a sampling device comprising a body into which there is arranged a space, which is provided with a sample port at its first end, a needle part arranged into the space to co-operate with the sample port, an actuator coupled to the needle part for positioning the needle to selectively open and close the sample port, where a needle part is arranged into a first body part of the sampling device and the actuator is arranged into a second body part, which needle part and actuator are arranged one after the other in common central axis in force transmission communication with each other.

However, taking samples during engine operation is cumbersome, difficult and requires more complexity to the engine structure. Due to even more stringent demands on efficiency and operational reliability, a need has emerged to improve the possibilities of tracking the operation of lubrication system and quality of lubrication oil on-line i.e. during the operation of the engine without the requirement of taking lubrication oil samples.

Thus, an easy to set-up, accurate, and highly functional and reliable solution is needed to provide more accurate system for determining remaining life of engine oil in an engine without requirement of taking oil samples from the engine.

SUMMARY

According to a first example aspect of the disclosed embodiments there is provided a computer implemented method for determining remaining life of engine oil in an engine, the method comprising:

determining reference engine parameters of a reference engine;

generating reference engine profile data based on the reference engine parameters;

determining reference engine oil lubrication data based on mechanical testing of an oil sample from the reference engine;

generating a reference model by associating the reference engine profile data with the reference engine oil lubrication data;

receiving the reference model at an engine apparatus;

measuring engine parameters of an engine of the engine apparatus; and determining remaining life of engine oil in the engine of the engine apparatus using the reference model and the engine parameters.

In an embodiment, the method further comprising:

receiving selection information for a plurality of reference engines; and generating the reference engine profile data by determining reference engine parameters of the plurality of reference engines based on the selection information.

In an embodiment, the method further comprising:

determining the reference engine parameters based on sensor data received from at least one reference engine.

In an embodiment, the reference engine parameters relate to different operation conditions of the reference engine. The reference engine parameters may relate to operational and environmental measurement data of the reference engine.

In an embodiment, the method further comprising:

determining the reference engine oil lubrication data based on mechanical testing of oil samples from the plurality of reference engines based on the selection information.

In an embodiment, the mechanical testing of the oil sample comprises tribological lubricity test of the oil sample.

In an embodiment, the tribological lubricity test is configured to be evaluated based on friction test rig results.

In an embodiment, the method further comprising:

determining the reference engine oil lubrication data based on the tribological lubricity test of the oil sample, wherein the reference engine oil lubrication data comprises Stribeck type of friction data.

In an embodiment, the method further comprising:

maintaining reference model data of the reference model at a server apparatus; and dynamically updating the reference model data in response to receiving reference engine profile data or reference engine oil lubrication data.

In an embodiment, the method further comprising:

transmitting engine apparatus identification information to the server apparatus;

generating the reference model by associating reference engine profile data with reference engine oil lubrication data based on the engine apparatus identification information; and receiving the generated reference model at an engine apparatus.

In an embodiment, the engine parameters relate to operational or environmental measurement data of the engine. The operational measurement data may comprise at least one of the following:

number of engine starts;
operating hours since last oil change;
load cycles of the engine;
miles traveled with the engine;
amount of fuel used by the engine; and
sensor data of the engine.

In an embodiment, the method further comprising:

associating the reference engine profile data with the reference engine oil lubrication data by combining to generate a function of the reference model.

In an embodiment, the method further comprising:

determining remaining life of the engine oil using the function of the reference model.

In an embodiment, the method further comprising:

determining current performance characteristics of the engine oil using the function of the reference model.

In an embodiment, the method further comprising:

determining predicted future performance characteristics of the engine oil using the function of the reference model.

In an embodiment, the reference model is received and the remaining life of engine oil in the engine of the engine apparatus are determined at the engine apparatus.

According to a second example aspect of the disclosed embodiments there is provided an engine apparatus, comprising:

an engine;
a communication interface;
at least one processor; and
at least one memory including computer program code;

the at least one memory and the computer program code configured to, with the at least one processor, cause the apparatus to:

receive a reference model, the reference model is configured to be generated by associating reference engine profile data with reference engine oil lubrication properties, wherein the reference engine profile data is configured to be generated by determining reference engine parameters relating to a different operation conditions of the reference engine, and the reference engine oil lubrication properties are configured to be determined for the different operation conditions based on mechanical testing of an oil sample from the reference engine;

measure engine parameters relating to operation conditions of the engine of the engine apparatus; and determine remaining life of engine oil in the engine of the engine apparatus using the reference model and the engine parameters.

According to a third example aspect of the disclosed embodiments there is provided a server apparatus comprising:

a communication interface;
at least one processor; and
at least one memory including computer program code;

the at least one memory and the computer program code configured to, with the at least one processor, cause the apparatus to:

generate a reference model by associating the reference engine profile data with the reference engine oil lubrication data, wherein the reference engine profile data is generated by determining reference engine parameters of a reference engine and the reference engine oil lubrication data is determined based on mechanical testing of an oil sample from the reference engine; and transmit the reference model to an engine apparatus for measuring engine parameters relating to operation conditions of an engine of the engine apparatus, and for determining remaining life of engine oil in the engine of the engine apparatus using the reference model and the engine parameters.

Different non-binding example aspects and embodiments of the disclosure have been illustrated in the foregoing. The above embodiments are used merely to explain selected aspects or steps that may be utilized in implementations of the present invention. Some embodiments may be presented only with reference to certain example aspects of the invention. It should be appreciated that corresponding embodiments may apply to other example aspects as well.

BRIEF DESCRIPTION OF THE DRAWINGS

The aspects of the disclosed embodiments will be described, by way of example only, with reference to the accompanying drawings, in which.

DETAILED DESCRIPTION

In the following description, like numbers denote like elements.

Figure 1:
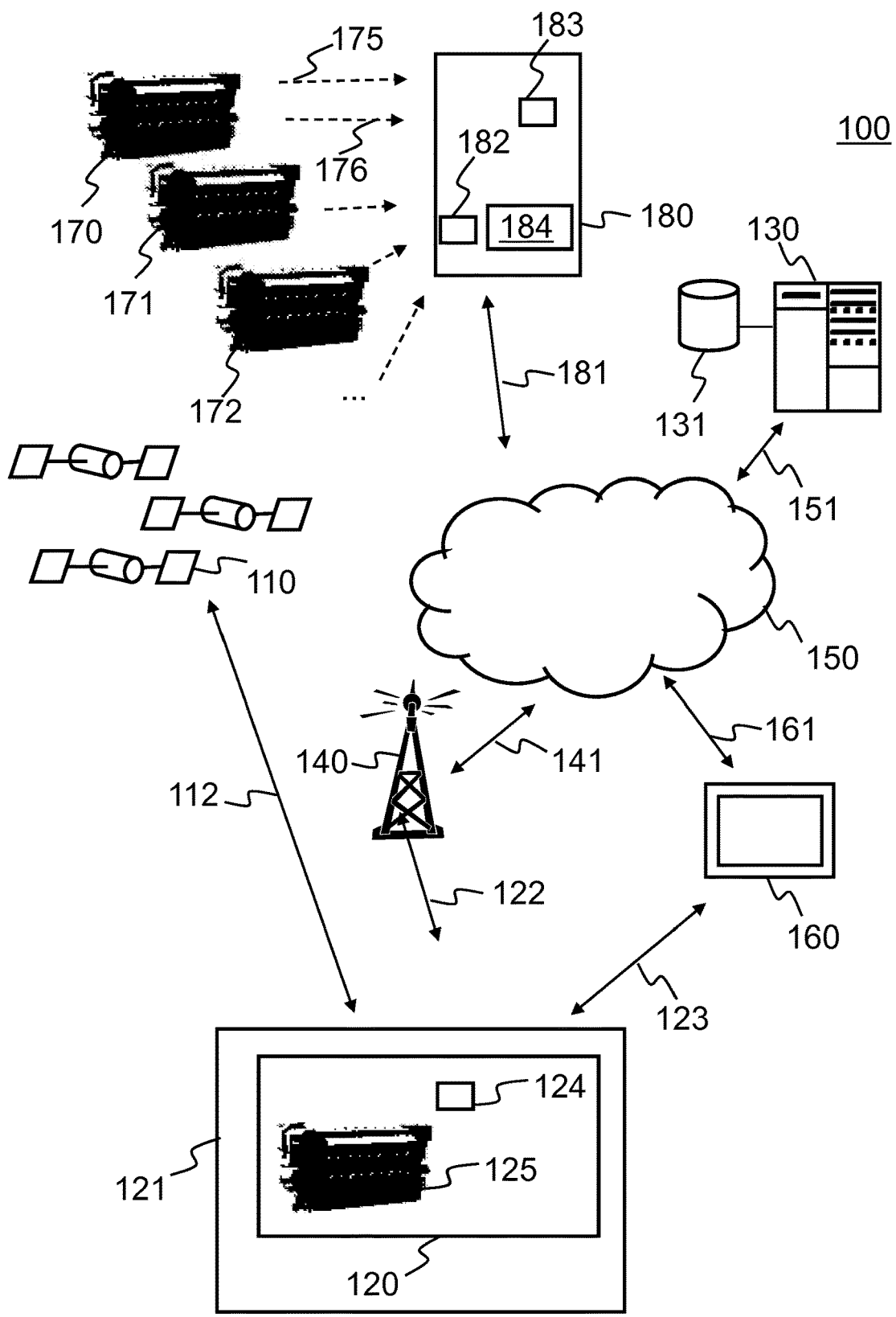
FIG. 1 shows a schematic picture of a system according to an aspect of the disclosed embodiments.

FIG. 1 shows a schematic picture of a system 100 according to an example embodiment. A marine vessel 121 or a power plant 121 may comprise an engine apparatus 120, for example. Instead of a marine vessel or a power plant, the system 121 may comprise any setup utilizing an engine with lubricant oil used for engine operation.

As an example, a marine vessel 121 is discussed. The marine vessel 121 comprises an engine apparatus 120 comprising means for generating, processing and transceiving engine related data through a communication interface, for example. The apparatus 120 is capable of downloading and locally executing software program code. The software program code may be a client application of a service whose possible server application is running on a server apparatus 130, 131 of the system 100. The apparatus 120 comprises an engine 125, a communication interface, a memory and a processor, and may further comprise a capturing device, such a sensor device, for providing engine related data 124. The sensor device may comprise an accelerometer, a gyroscope, a temperature sensor, a pressure sensor, a measuring sensor or a camera, for example. The camera may also be used to provide video data and a microphone may be used for providing audio data, for example.

In an embodiment, there is provided a computer implemented method, apparatus and system for determining remaining life of engine oil in an engine 125 of the engine apparatus 120. At least one reference engine 170-172 is configured to generate reference engine profile data 182 by determining reference engine parameters 175 of the reference engine 170-172. At least one reference engine 170-172 is configured to generate reference engine oil lubrication data 183 by mechanical testing of an oil sample 176 from the reference engine 170-172. Reference engine 170-172 related measurements, data collection and transceiving may be carried out by a reference engine data apparatus 180. A reference model 184 is generated by associating the reference engine profile data 182 with the reference engine oil lubrication data 183.

The reference model 184 may be transmitted to a server apparatus 130, 131 for storing and processing over connection 181. The reference engine profile data 182 and/or the reference engine oil lubrication data 183 may also be transmitted to a server apparatus 130, 131 for storing and processing. The reference model 184 may also be generated at the server apparatus 130, 131.

The reference model 184 is configured to be received at an engine apparatus 120 that may comprise on-site engine 125 or engine 125 operated in the marine vessel 121, for example. At the engine apparatus 120, engine parameters 124 are measured relating to operation conditions of an engine 125 of the engine apparatus 120, and remaining life of engine oil in the engine 125 of the engine apparatus 120 is determined using the reference model 184 and the engine parameters 124.

In the present description, by vessel are meant any kinds of waterborne vessels, typically marine vessels. Most typically the vessel is a cargo ship or large cruise vessel, but the present disclosure is also applicable for yachts, for example. In the present description, by power plant are meant any kinds of power generating systems, typically power plants with a power producing combustion engine 125, such as an LNG engine or a diesel engine or a hybrid engine. Most typically the power plant is a multi-source plant implementing also solar, wind or battery management system, but the present disclosure is also applicable for any system comprising an engine with lubricant oil.

The engine apparatus 120 is configured to be connectable at least occasionally to a public network 150, such as Internet, directly via local connection or via a wireless communication network 140 over a wireless connection 122. The wireless connection 122 may comprise a mobile cellular network, a satellite network or a wireless local area network (WLAN), for example. The wireless communication network 140 may be connected to a public data communication network 150, for example the Internet, over a data connection 141. The engine apparatus 120 may be configured to be connectable to the public data communication network 150, for example the Internet, directly over a data connection that may comprise a fixed or wireless mobile broadband access. The wireless communication network 140 may be connected to a server apparatus 130 of the system 100, over a data connection.

In an embodiment, an engine apparatus 120 may set up local connections within the marine vessel 121 (or power plant, for example) with at least one capturing device, such as a sensor, and a computer device. The capturing device, such as a sensor, may be integrated to the engine apparatus 120 or the marine vessel 121, attached to the hull of the marine vessel 121 and connected to the vessel control system or arranged as separate sensor device and connectable to the network 150 over separate connection.

The engine apparatus 120 and its client application may allow the engine apparatus 120 to log into a vessel or engine data service run on a server 130, for example.

Real-time interaction may be provided between the engine apparatus 120 and the server 130 to collaborate for marine vessel data over a network 150. Real-time interaction may also be provided between the engine apparatus 120 and the remote user device 160 to collaborate for marine vessel or engine data over a network 150, 161.

A sensor data item, such as engine parameters 124, is generated by a sensor device of the marine vessel 121 and transmitted to the server 130. Sensor data items may be processed at the engine apparatus 120 before transmitting or they may be sent without further processing to the server 130.

Sensor data may also be stored within the engine apparatus 120 before transmission over the network 150. Then again, transmitted sensor data may be stored/and or processed at the server apparats 130 or at the remote user device 160.

A capturing device (e.g. a sensor device) may capture and send sensor data as a real-time content or non-real time data to the server apparatus 130 or to the remote user device 160 over a peer-to-peer connection formed over network, for example.

The engine apparatus 120 may be connected to a plurality of different capturing devices and instruments and the engine apparatus 120 may be configured to select which sensor device(s) is actively collaborated with.

The user of the engine apparatus 120 or the remote user device 160 may need to be logged in with user credentials to a chosen service of the network server 130.

In an embodiment, the system 100 comprises a sensor device configured to be comprised by or connectable to the engine apparatus 120 over a local connection. The local connection may comprise a wired connection or a wireless connection. The wired connection may comprise Universal Serial Bus (USB), High-Definition Multimedia Interface (HDMI), or RCA interface, for example. The wireless connection may comprise acoustic connection, Bluetooth™, Radio Frequency Identification (RF-ID) or wireless local area network (WLAN), for example. Near field communication (NFC) may be used for sensor device identification between the sensor device and the engine apparatus 120, for example.

A sensor device may also be connected directly to the public network 150, such as Internet, via direct local connection or via a wireless cellular network connection 140, 141.

In an embodiment, the system 100 may comprise a server apparatus 130, which comprises a storage device 131 for storing service data, service metrics and subscriber information, over data connection 151. The service data may comprise configuration data; account creation data; sensor data; sensor ID's; reference data items, user input data; real-time collaboration data; reference engine profile data, reference engine parameters, reference engine oil lubrication data, predefined settings; and attribute data, for example.

In an embodiment, a proprietary application in the engine apparatus 120 may be a client application of a service whose server application is running on the server apparatus 130 of the system 100.

The proprietary application of the engine apparatus 120 may receive sensor input data and provide the output data. The input data may comprise data captured by the capturing device, such as a sensor device or a camera.

In an embodiment, configuration information or application download information for any apparatus may be automatically downloaded and configured by the server 130. Thus, the user of the devices may not need to do any initialization or configuration for the service. The system server 130 may also take care of account creation process for the service, sensor devices, apparatuses and users.

In an embodiment, the association of the devices can be one-time or stored persistently on any of the devices or the server 130.

In an embodiment, authentication of a sensor device or engine apparatus 120 on a system server 130 may utilize hardware or SIM credentials, such as International Mobile Equipment Identity (IMEI) or International Mobile Subscriber Identity (IMSI). The sensor device or engine apparatus 120 may transmit authentication information comprising IMEI and/or IMSI, for example, to the system server 130. The system server 130 authenticates the device or engine apparatus 120 by comparing the received authentication information to authentication information of registered users/devices/vessels/apparatuses stored at the system server database 131, for example. Such authentication information may be used for pairing the devices and/or apparatuses to generate association between them for a vessel or power plant data connection.

In an embodiment, a service web application may be used for configuration of a system. The service web application may be run on any user device, admin device, or a remote control device 160, such as a personal computer connected to a public data network, such as Internet 150, for example. The control apparatus 160 may also be connected locally to the engine apparatus 120 over a local connection 123 and may utilize the network connections of the apparatus 120 for configuration purposes. The service web application of the control apparatus 160 may provide searching/adding instruments, determining attributes, device setup and configuration, for example. The service web application of the control apparatus 160 may be a general configuration tool for tasks being too complex to be performed on the user interface of the engine apparatus 120, for example.

In an embodiment, a remote control apparatus 160 may be authenticated and configuration data sent from the control apparatus 160 to the system server 130, 131, wherein configuration settings may be modified based on the received data. In an embodiment, the modified settings may then be sent to the engine apparatus 120 over the network 150 and the local connection or the wireless operator. The modified settings may also be sent to external devices correspondingly, through the engine apparatus 120 or directly over the network 150, for example.

In an embodiment, the sensor device may be wireless or wired.

The system 100 may also comprise a plurality of satellites 110 in orbit about the Earth. The orbit of each satellite 110 is not necessarily synchronous with the orbits of other satellites and, in fact, is likely asynchronous. A global positioning system receiver apparatus such as the ones described in connection with preferred embodiments of the present invention is shown receiving spread spectrum global positioning system (GPS) satellite signals 112 from the various satellites 110. The plurality of satellites 110 may be used for location purposes, input for determining traveled distance (since oil change, for example), or input for accurate time (since oil change, for example).

The remote control apparatus 160 may be configured to be operated by a remote operator of the vessel 121. The remote control apparatus 160 may be arranged on a ground station, on the vessel 121 or on another vessel, for example.

Figure 2:
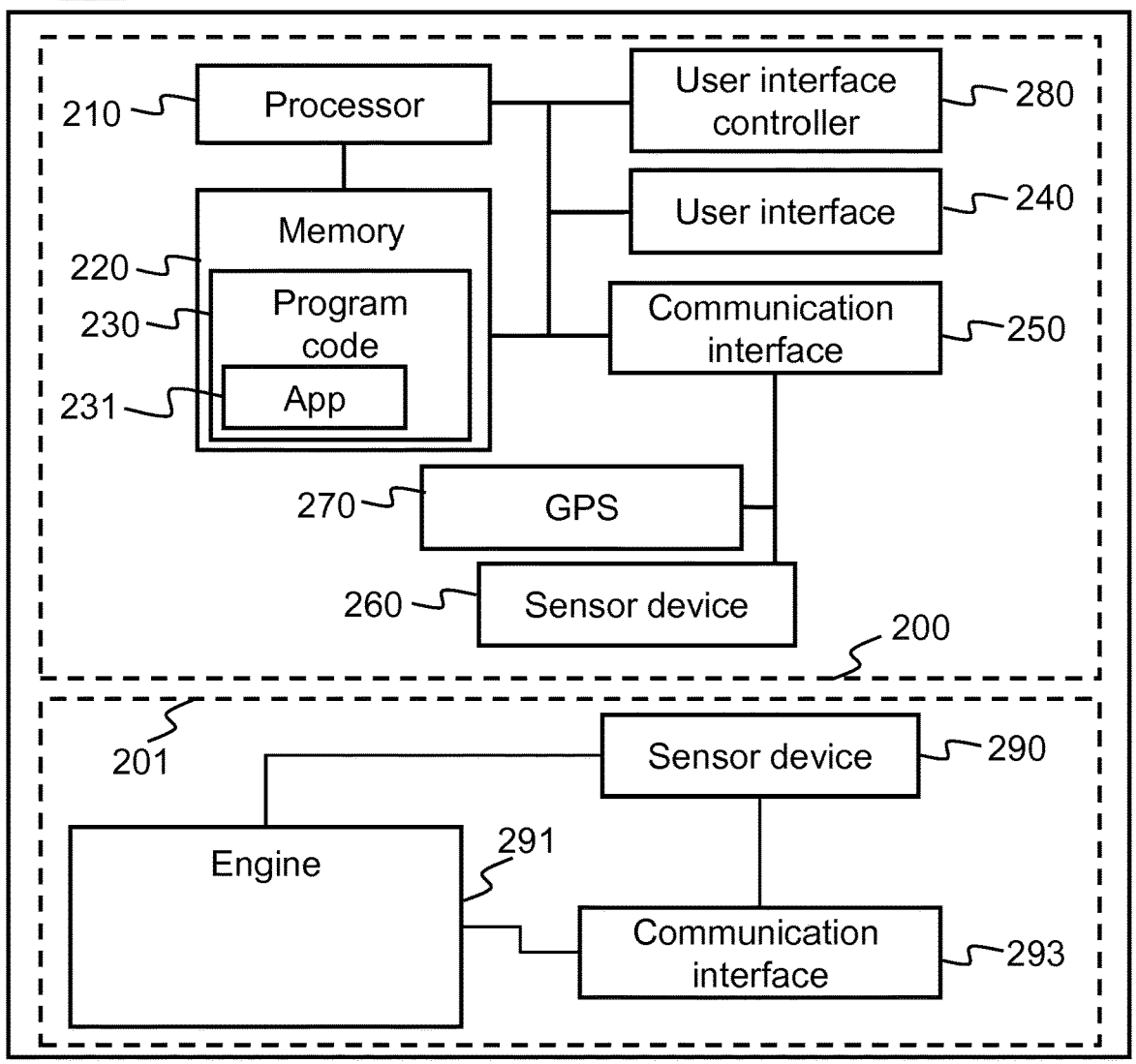
FIG. 2 presents an example block diagram of an engine apparatus (marine vessel or power plant) in which various embodiments of the invention may be applied.

FIG. 2 presents an example block diagram of an engine apparatus 120 (within a marine vessel or a power plant, for example) in which various embodiments of the invention may be applied. The engine apparatus 120 may comprise a user equipment (UE), user device or apparatus, such as a vessel computer system, in addition to the engine.

The general structure of the engine apparatus 120 comprises a control unit 200 and an engine unit 201.

The general structure of the control unit 200 may comprise a user interface 240, a communication interface 250, a satellite positioning device (GPS) 270, a capturing/sensor device 260 for capturing current activity data and/or current environmental data relating to the vessel or the power plant, a processor 210, and a memory 220 coupled to the processor 210. The control unit 200 further comprises software 230 stored in the memory 220 and operable to be loaded into and executed in the processor 210. The software 230 may comprise one or more software modules and can be in the form of a computer program product. The control unit 200 may further comprise a user interface controller 280.

The processor 210 may be, e.g., a central processing unit (CPU), a microprocessor, a digital signal processor (DSP), a graphics processing unit, or the like. FIG. 2 shows one processor 210, but the apparatus 120 may comprise a plurality of processors.

The memory 220 may be for example a non-volatile or a volatile memory, such as a read-only memory (ROM), a programmable read-only memory (PROM), erasable programmable read-only memory (EPROM), a random-access memory (RAM), a flash memory, a data disk, an optical storage, a magnetic storage, a smart card, or the like. The apparatus 120 may comprise a plurality of memories. The memory 220 may be constructed as a part of the apparatus 120 or it may be inserted into a slot, port, or the like of the apparatus 120 by a user. The memory 220 may serve the sole purpose of storing data, or it may be constructed as a part of an apparatus serving other purposes, such as processing data. A proprietary oil lifetime data application (client application) 231 comprising the reference model is stored at the memory 220. Engine data, sensor data and environmental data may also be stored to the memory 220.

The user interface controller 280 may comprise circuitry for receiving input from a user of the apparatus 120, e.g., via a keyboard, graphical user interface shown on the display of the user interfaces 240 of the engine apparatus 120, speech recognition circuitry, or an accessory device, such as a headset, and for providing output to the user via, e.g., a graphical user interface or a loudspeaker.

The satellite positioning device 270 is configured to provide location information or time information, for example. Such information may comprise, for example, position coordinates, speed, direction of movement, GPS time; and altitude information.

The communication interface module 250 implements at least part of data transmission. The communication interface module 250 may comprise, e.g., a wireless or a wired interface module. The wireless interface may comprise such as a WLAN, Bluetooth, infrared (IR), radio frequency identification (RF ID), GSM/GPRS, CDMA, WCDMA, LTE (Long Term Evolution), or 5G radio module. The wired interface may comprise such as universal serial bus (USB) or National Marine Electronics Association (NMEA) 0183/2000 standard for example. The communication interface module 250 may be integrated into the apparatus 120, or into an adapter, card or the like that may be inserted into a suitable slot or port of the apparatus 120. The communication interface module 250 may support one radio interface technology or a plurality of technologies. The apparatus 120 may comprise a plurality of communication interface modules 250.

A skilled person appreciates that in addition to the elements shown in FIG. 2, the apparatus 120 may comprise other elements, such as microphones, extra displays, as well as additional circuitry such as input/output (I/O) circuitry, memory chips, application-specific integrated circuits (ASIC), processing circuitry for specific purposes such as source coding/decoding circuitry, channel coding/decoding circuitry, ciphering/deciphering circuitry, and the like. Additionally, the apparatus 120 may comprise a disposable or rechargeable battery (not shown) for powering when external power if external power supply is not available.

In an embodiment, the apparatus 120 comprises speech recognition means. Using these means, a pre-defined phrase may be recognized from the speech and translated into control information for the apparatus 120, for example.

The satellite positioning device 270 and the sensor device 260 may be configured to be comprised by the apparatus 120 or connected as separate devices to the apparatus 120. In case the satellite positioning device 270 and the capturing device 260 are comprised in the apparatus 120 they may be connected to the apparatus 120 using an internal bus of the apparatus 120. In case the satellite positioning device 270 and the sensor device 260 are external devices connected to the apparatus 120 they may be connected to the apparatus 120 using communication interface 250 of the apparatus 120 or using the internal bus.

The general structure of the engine unit 201 may comprise an engine 291, another sensor device 290 and a communication interface 293. The sensor device 290 may be not necessarily connected to the internal bus and to the main processor 210 and memory 220. Such sensor device 290 may be connected to the engine 291 and the communication interface 293 of the engine unit 201. Furthermore, sensor data items with sensor data provided by the sensor device 290 may be transmitted over the communication interface 293. Alternatively, sensor data items with sensor data provided by the sensor device 290 may be provided for and transmitted by the communication interface 250.

In an embodiment, a second sensor device 260 may be configured to be integrated to a marine vessel's 121 information system 200, and the first sensor device 290 is configured not to be integrated to the marine vessel's 121 information system 200 but to the engine 291 only.

In an embodiment, the first sensor device 290 is configured to be integrated to the engine 291 of the engine apparatus 120.

No matter a single sensor 290 is shown, the sensor 290 may comprise a plurality of sensors 290. The sensor devices 290 may be configured to, for example, measure engine performance or operational data.

In an embodiment, a communication interface (see e.g., FIG. 3) of the sensor device 290 itself or the communication interface 293 of the engine unit 201 comprises an automatic identification system (AIS) receiver for receiving a wireless transmission comprising automatic identification system data from the marine vessel 121. The AIS receiver may include an antenna configured to receive the automatic identification system data or the sensor device 290 may include an antenna configured to receive the automatic identification system data. In another example, AIS receiver is configured to receive the automatic identification system data from an antenna external to the sensor device 290.

In an embodiment, the engine 291 and at least one sensor device 290 are configured to generate sensor data items based on the received automatic identification system data and sensor data. The sensor data item may thus comprise sensor data generated by the sensor device 290 and an identifier information. The identifier information may comprise at least one of the following: sensor-ID (S-ID); engine-ID (E-ID), and vessel-ID (V-ID) (see also FIG. 11) that comprises at least part of the received automatic identification system data.

The sensor data item may also comprise information identifying the marine vessel (for example, International Maritime Organization (IMO) ship identification number or Maritime Mobile Service Identity (MMSI)). This identifying information may be taken from the automatic identification system (AIS) signal or it may be stored within the engine apparatus 120 when installed.

The sensor data relating to the engine 291 performance and operation measured by the at least one sensor device 260, 290 or GPS 270 may comprise measured data values as they were measured and/or data after processing at least some of the measured data values first.

In an embodiment, universal clock information of the control unit 200 is determined based on a vessel receiver device, comprising at least one of the Global Positioning System (GPS) receiver 270 and a communication interface 250 of the marine vessel. The universal clock information may comprise at least one of the following: a Global Positioning System (GPS) time and a Coordinated Universal Time (UTC).

In an embodiment, it is provided a method for determining the speed through water of the marine vessel for optimisation of vessel operation, using a sensor system with a plurality of sensors comprising at least one first sensor 290 of a first type and at least one second sensor 260, 270 of a second type 260, 270. The method comprises obtaining propeller revolutions per minute and at least one of torque at propeller, propulsion power, thrust, and engine fuel consumption using at least one first sensor 290, obtaining speed over ground of the vessel using at least one second sensor 260, 270; and using the obtained data and hydrodynamic modeling to determine the speed through water of the vessel. The sensor data may be sent to the server apparatus as raw sensor data and the processing of the data and determination of vessel data may be carried out at the server. Additional first sensors 290 may be used, for example, to provide wind and sea state information that can also be used for determining vessel data, such as speed through water (STW). Traditionally, optimising operation of the vessel has been carried out using the STW measured by an STW log, which is inadequate due to calibration and noise issues. Hydrodynamic modeling data may be maintained at the control unit 200, e.g. in memory 220, and the hydrodynamic modeling data may be updated and downloaded from the server apparatus 130 over the network 150 when access is available, such as when docked in a harbor, for example.

In an embodiment, a proprietary oil lifetime data application (client application) comprising the reference model 231 is received at an engine apparatus control unit 200 from the server apparatus, for example. Engine parameters relating to operation conditions of an engine 291 of the engine apparatus 120 are measured using at least one sensor 260, 290. Remaining life of engine oil in the engine 291 of the engine apparatus 120 is then determined using the reference model 231 and the engine parameters.

In an embodiment, at least one of the propeller revolutions per minute, torque at propeller, propulsion power, thrust, and engine fuel consumption is a measurement value resulting from a corresponding indirect measurement based on vessel vibrations, and can be used as further input for the reference model 231.

For at least one first sensor 290, instead of a direct measurement of for example the propeller revolutions, it is possible to obtain this measurement value or data from an indirect measurement based on vessel vibrations detected by the sensor 290 attached to the vessel hull or engine, for example.

No matter a plurality of elements is shown, all elements are not essential for all embodiments. Some elements are optional, such as GPS 270, sensor device 260, user interface 240 and user interface controller 280.

Figure 3:
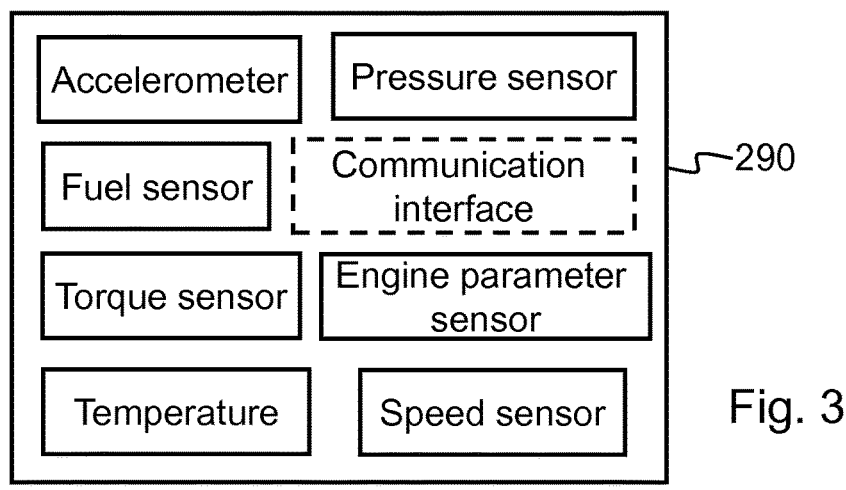
FIG. 3 presents an example block diagram of a sensor device in accordance with an example embodiment.

FIG. 3 presents an example block diagram of a sensor device 260, 290 in which various embodiments of the invention may be applied. The sensor device 260, 290 may comprise various means for activity data detection, operational data detection and environmental data detection, for example. The sensor device 260, 290 may be used for both engine related data and environmental data capturing. The sensor device 260 may correspond to the sensor device 290 elements illustrated in FIG. 3.

In an embodiment, the sensor device 260, 290 and the processing of the sensor data may provide a plurality of parameters relating to an engine, for example one or more of the following: time, position (latitude & longitude), SOG (speed over ground), COG (course over ground), vibrations in three dimensions, propeller/engine RPM the operation conditions of the engine comprises at least one of the following: number of engine starts; operating hours since last oil change; load cycles of the engine; miles traveled with the engine; amount of fuel used by the engine; and integral sensor data of the engine.

The sensor device 290 may also comprise several capturing devices, combinations of any above-mentioned devices, and the like. The environmental temperature may comprise air temperature, water temperature or ground surface temperature, for example.

The sensor device 290 may comprise also a communication interface capable of connecting with at least one of the communication interfaces 250, 293. The generated sensor data may be transmitted to the communication interface 293. The sensor device 290 may also transmit its sensor data via its internal communication interface to the communication interface 250 of the control unit 200.

In an embodiment, the communication interface within the sensor device 290 or the communication interface 293 is, for example, a wireless transmitter or a wireless transceiver (for example, Wireless Local Area Network (WLAN) transceiver or any mobile or cellular communication network transceiver (for example, Wideband Code Division Multiple Access (WCDMA), Long Term Evolution (LTE) etc.) or a local data port (e.g. Ethernet, Universal Serial Bus (USB) etc.).

In an embodiment, the sensor device 290 may also store information identifying the engine, the marine vessel or the power plant. This may have been preconfigured to the sensor device 290. Since the automatic identification system data identifies e.g. the marine vessel to which the received data relates to, the sensor device 290 is thus able to make sure that the received automatic identification system data relates to the marine vessel to which the sensor device 290 is affixed. One possibility for identifying the correct marine vessel is to use, for example, wireless signal strength of the AIS signal. The strongest AIS signal relates to the marine vessel to which the sensor device 290 is attached. Yet another possibility is to compare the acceleration signal from the acceleration sensor to the data indicating vessel movements in the AIS signals and to determine the correct AIS signal based on the comparison.

A second sensor device 260 of the marine vessel main information system 200 may comprise corresponding elements as disclosed for the first sensor device 290.

In an embodiment, a sensor device 290 is configured to measure the marine vessel performance related data when the sensor device 290 is affixed to the hull structure of the marine vessel 121. For example, bolting, gluing or any other way for affixing or attaching the sensor device 290 to the hull structure or engine body may be used. In other words, since the sensor device 290 is firmly attached to the hull structure or engine body, there is no relative motion between the sensor device 290 and the hull structure or engine body respectively, and thus the sensor or sensors 290 sense the motions and vibrations of marine vessel or the engine via the hull structure or the engine body.

The AIS receiver (comprised by the communication interface 293 or the communication interface within the sensor device 290) may receive a wireless transmission comprising an AIS signal from the same marine vessel 121 to which the sensor device 290 is affixed. The sensor device 290 may beforehand store information identifying the marine vessel 121 (for example, International Maritime Organization (IMO) ship identification number or Maritime Mobile Service Identity (MMSI)) so that it is able to determine that the AIS signal relates to the marine vessel 121 to which it is affixed. The AIS signal includes several pieces of information relating to the marine vessel, for example, the vessel's identity, engine(s) identifier(s) and type, position, course, speed, navigational status and other related information. The sensor device 290 may utilize the AIS signal as it was received (in other words, every piece of information contained in the AIS signal). In another example, the sensor device 290 may select a subset of information included in the AIS signal to be included in the sensor data. In one example, the subset includes at least position and/or time information of the marine vessel 121.

Normally the AIS signal is intended to assist a vessel's watch standing officers to track and monitor movements of other vessels and also allow maritime authorities to track and monitor movements of vessels. It also identifies and locates vessels by electronically exchanging data with other nearby ships.

In an embodiment, the AIS signal is received by a sensor device 290 installed in a vessel that is sending the AIS signal. This makes it possible for the sensor device to link the AIS signal with sensor data measured by the sensor or sensors 290. Since the sensor device 290 has the information included in the AIS signal and measurements from one or more sensors 290, there is no need to make the traditional integration tasks to the marine vessel's information systems. The AIS signal sent by the marine vessel to the sensor device 290 is a strong signal. Therefore, it may not be necessary to install a separate antenna in order to be able to receive the AIS signal. This makes the installation of the sensor device 290 simpler and quicker. For example, it is possible to install the sensor device 290 including only an internal antenna inside a marine vessel because the AIS signal leaks to the interior of the marine vessel via various existing cables, for example.

In an embodiment, a video camera is configured to provide video signal. Based on the video signal the apparatus may determine at least part of the environmental or operational data. The determination may be done by video image processing, pattern recognition, filtering or other such means, for example.

The sensor device 260, 290 may comprise communication interface module implementing at least part of data transmission. The communication interface module may comprise, e.g., a wireless or a wired interface module. The wireless interface may comprise such as a WLAN, Bluetooth, infrared (IR), radio frequency identification (RF ID), GSM/GPRS, CDMA, WCDMA, or LTE (Long Term Evolution) radio module. The wired interface may comprise such as universal serial bus (USB) or National Marine Electronics Association (NMEA) 0183/2000 standard for example. The communication interface module may be integrated into the sensor device 260, 290 or into an adapter, card or the like that may be inserted into a suitable slot or port of the sensor device 260, 290. The communication interface module may support one radio interface technology or a plurality of technologies. The sensor device 260, 290 may comprise a plurality of communication interface modules.

The sensor device 290 disclosed in FIGS. 2-3 may include at least one accelerometer or three-dimensional accelerometer. Since the sensor device 290 may be affixed to the hull of the marine vessel or the engine body, the accelerometer is able to sense vibrations in the hull of the body. From the vibrations sensed by the accelerometer, it is possible to determine, for example, speed of rotation of a propeller of the marine vessel or of the main engine. In most vessels, the speed of rotation of the propeller is identical with the speed of rotation of an engine of a marine vessel. Thus, it is possible to determine, based on an analysis of the measurements of the accelerometer, the speed of rotation of a propeller and an engine of a marine vessel.

In an embodiment, in order to determine the speed of rotation of the propeller, the sensor device 290 or the associated computer device may analyze the signals measured by the accelerometer to identify the fundamental frequency in the signals. The fundamental frequency is the RPM (Revolutions Per Minute) of the engine or its multiple. One possible method for pitch detection (i.e. find the fundamental frequency) is the Harmonic Product Spectrum (HPS) method. In the method, a spectrum is compressed a number of times (down sampling), and it is compared with the original spectrum. It can then be seen that the strongest harmonic peaks line up. The first peak in the original spectrum coincides with the second peak in the spectrum compressed by a factor of two, which coincides with the third peak in the spectrum compressed by a factor of three. Hence, when the various spectrums are multiplied together, the result will form a clear peak at the fundamental frequency. It is obvious that the HPS is only one possible method for finding the fundamental frequency and also other methods may be used. The speed of rotation of the propeller may also be stored in the memory of the sensor device 290 to be transmitted to or accessed by an external entity.

Furthermore, device or apparatus analyzing the sensor data, such as a server apparatus 130, the sensor device itself, the control unit 200 or the remote apparatus 160 may perform frequency analysis of the signals measured by at least one acceleration sensor of the sensor device 290. In case the sensor device or some other device or apparatus performs the frequency analysis, the amount of sensor data to be transmitted outside the sensor device/computer device is reduced. The frequency analysis may comprise, for example, frequency-time analysis, such as Short-Time Fourier Transform (STFT) or Discrete Wavelet Transform (WFT). With the frequency analysis, an understanding of frequency components over a short time is received. The frequency analysis is performed, for example, so that motions of a marine vessel 121 can be understood better and also analyzed.

Further, the frequency analysis may comprise applying a dimensionality reduction method, for example, Principal Component Analysis (PCA) in order to identify the most significant components in the frequency domain.

An accelerometer and an inclinometer can be used to measure the same parameters since both of them measure acceleration. One of the main differences is that the accelerometer provides acceleration components separately, but they are more inaccurate. However, acceleration components are usually provided within a larger dynamic range. The inclinometer measures inclination more accurately but within a narrower range. Therefore, it is possible to perform RPM measurements also with the inclinometer if its bandwidth is high enough. Further, it may be possible to perform a frequency analysis for the data provided by the inclinometer and get the same or almost the same results than based on accelerometer data. One difference, however, is that the inclinometer does not measure vertical acceleration.

Based on the analysis of the sensor data, it may be possible to determine the operation efficiency of the marine vessel 121 (or the power plant, for example) and its engine 120 and to automatically trigger service requests such as oil change for the engine 120, for example.

Based on the information available and generated by the sensor device 260, 290 it may be possible to optimize and analyze various factors relating to energy efficiency of a marine vessel using the reference model 231.

Marine vessel data and engine data may be generated based on received sensor data from at least one sensor. Based on the engine data and the reference model 231 it is possible to determine performance optimization. Sensor detected engine data may also be transmitted to the server apparatus 130, 131 and utilize the data and the reference model 231 there for calculation of optimized oil-change time, for example.

Figure 4:
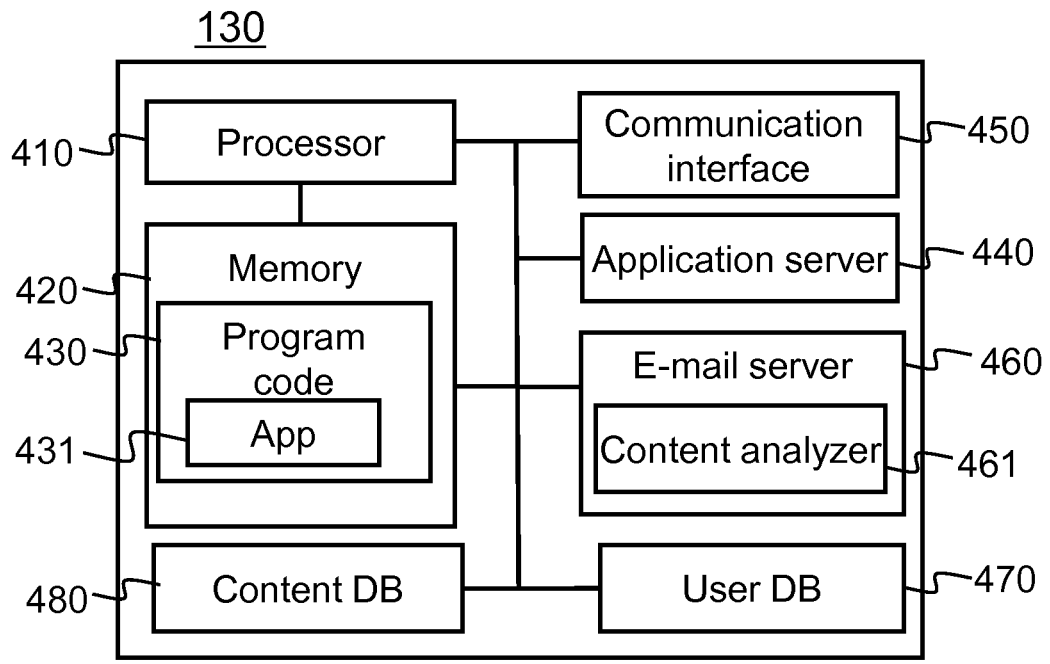
FIG. 4 presents an example block diagram of a server apparatus in accordance with an example embodiment.

FIG. 4 presents an example block diagram of a server apparatus 130 in which various embodiments of the invention may be applied.

The general structure of the server apparatus 130 comprises a processor 410, and a memory 420 coupled to the processor 410. The server apparatus 130 further comprises software 430 stored in the memory 420 and operable to be loaded into and executed in the processor 410. The software 430 may comprise one or more software modules, such as service application 431 and can be in the form of a computer program product.

The processor 410 may be, e.g., a central processing unit (CPU), a microprocessor, a digital signal processor (DSP), a graphics processing unit, or the like. FIG. 4 shows one processor 410, but the server apparatus 130 may comprise a plurality of processors.

The memory 420 may be for example a non-volatile or a volatile memory, such as a read-only memory (ROM), a programmable read-only memory (PROM), erasable programmable read-only memory (EPROM), a random-access memory (RAM), a flash memory, a data disk, an optical storage, a magnetic storage, a smart card, or the like. The server apparatus 130 may comprise a plurality of memories. The memory 420 may be constructed as a part of the server apparatus 130 or it may be inserted into a slot, port, or the like of the server apparatus 130 by a user. The memory 420 may serve the sole purpose of storing data, or it may be constructed as a part of an apparatus serving other purposes, such as processing data.

The communication interface module 450 implements at least part of radio transmission. The communication interface module 450 may comprise, e.g., a wireless or a wired interface module. The wireless interface may comprise such as a WLAN, Bluetooth, infrared (IR), radio frequency identification (RF ID), GSM/GPRS, CDMA, WCDMA, LTE (Long Term Evolution), or 5G radio module. The wired interface may comprise such as universal serial bus (USB) or National Marine Electronics Association (NMEA) 0183/ 2000 standard for example. The communication interface module 450 may be integrated into the server apparatus 130, or into an adapter, card or the like that may be inserted into a suitable slot or port of the server apparatus 130. The communication interface module 450 may support one radio interface technology or a plurality of technologies. Captured activity data associated with environmental data of the engine apparatus 120 (e.g. from marine vessel or from power plant), as well as measured engine parameters relating to operation conditions of the engine of the engine apparatus may be received by the server apparatus 130 using the communication interface 450.

The e-mail server process 460, which receives e-mail messages sent from engine apparatuses 120, such as marine vessel or power plant apparatuses, and remote computer apparatuses 160 via the network 150. The server 460 may comprise a content analyzer module 461, which checks if the content of the received message meets the criteria that are set for new activity data item of the service. The content analyzer module 461 may for example check whether the e-mail message contains a valid activity data item to be used as reference data item. The valid reference data item received by the e-mail server is then sent to an application server 440, which provides application services e.g. relating to the user accounts stored in a user database 470 and content of the content management service. Content provided by the service system 100 is stored in a content database 480.

A skilled person appreciates that in addition to the elements shown in FIG. 4, the server apparatus 130 may comprise other elements, such as microphones, displays, as well as additional circuitry such as input/output (I/O) circuitry, memory chips, application-specific integrated circuits (ASIC), processing circuitry for specific purposes such as source coding/decoding circuitry, channel coding/decoding circuitry, ciphering/deciphering circuitry, and the like. Not all elements disclosed in FIG. 4 are mandatory for all embodiments.

According to an embodiment, reference engine profile data and reference engine oil lubrication data may be received at the server apparatus 130, wherein the reference engine profile data is generated by determining reference engine parameters of a reference engine, and the reference engine oil lubrication data is determined based on mechanical testing of an oil sample from the reference engine. A reference model may be generated at the server apparatus 130 by associating the reference engine profile data with the reference engine oil lubrication data. The reference model or an engine-specific modified version of it is transmitted to the engine apparatus 120, where engine parameters 125 relating to operation conditions of the engine 125 of the engine apparatus 120 is measured, and remaining life of engine oil in the engine 125 of the engine apparatus 120 may be determined using the reference model and the engine parameters.

According to an embodiment, the server apparatus 130 may receive selection information for a plurality of reference engines and generate the reference engine profile data by determining reference engine parameters of the plurality of reference engines based on the selection information. The reference engine parameters may be generated based on sensor data received from at least one reference engine. The reference engine parameters may relate to different operation conditions of the reference engine.

In an embodiment, a reference engine data apparatus 180 (see FIG. 1) may be configured to determine the reference engine oil lubrication data based on mechanical testing of oil samples from the plurality of reference engines based on the selection information. The mechanical testing of the oil sample, carried out by the reference engine data apparatus 180, comprises tribological lubricity test of the oil sample. The tribological lubricity test may be configured to be evaluated based on friction test rig results.

In an embodiment, the reference engine oil lubrication data is based on the tribological lubricity test of the oil sample, wherein the reference engine oil lubrication data comprises Stribeck type of friction data.

The reference model data of the reference model may be maintained at a server apparatus 130, and dynamically updating the reference model data in response to receiving reference engine profile data or reference engine oil lubrication data.

In an embodiment, the server apparatus 130 receives engine apparatus identification information and generates the reference model by associating reference engine profile data with reference engine oil lubrication data based on the engine apparatus identification information. The generated reference model may be transmitted to the engine apparatus 120 for determining engine current and future performance, as well as estimating engine oil lifetime.

Figure 5:
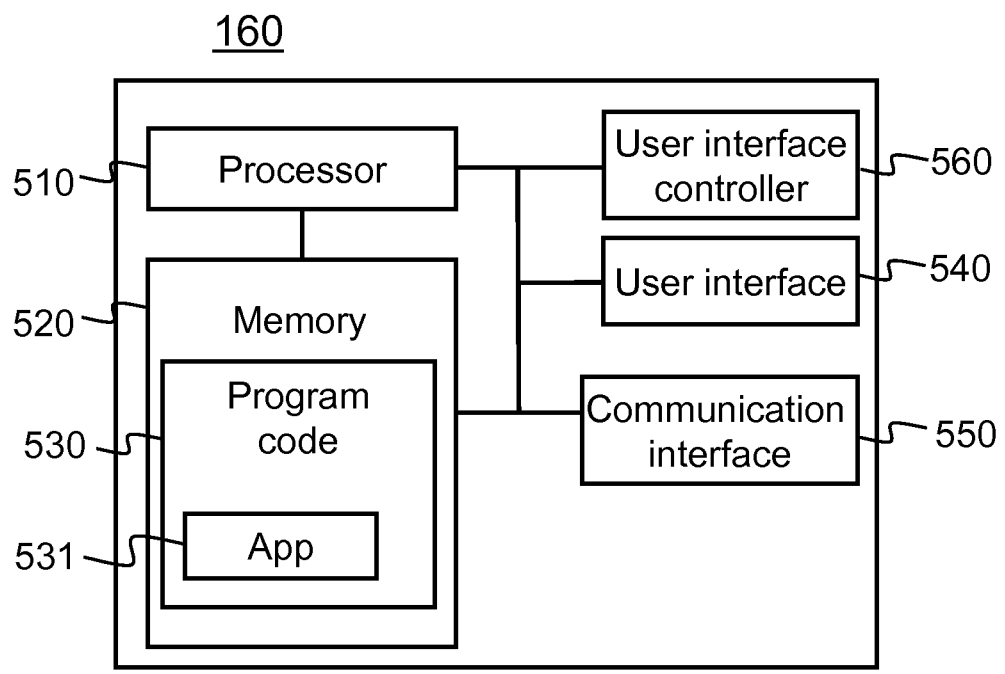
FIG. 5 presents an example block diagram of a remote computer apparatus.

FIG. 5 presents an example block diagram of a remote computer apparatus 160 in which various embodiments of the invention may be applied. The computer apparatus 160 may be a user equipment (UE), user device or apparatus, such as a mobile terminal, a smart phone, a laptop computer, a desktop computer or other communication device. The remote control apparatus 160 may be configured to be operated by a remote operator of the vessel 121 or the power plant 121 (FIG. 1). The remote control apparatus 160 may be arranged on a ground station, on the vessel 121 (FIG. 1) or on another vessel, for example.

The general structure of the computer apparatus 160 comprises a user interface 540, a communication interface 550, a processor 510, and a memory 520 coupled to the processor 510. The computer apparatus 160 further comprises software 530 stored in the memory 520 and operable to be loaded into and executed in the processor 510. The software 530 may comprise one or more software modules, such as remote client software application 531, and can be in the form of a computer program product. The computer apparatus 160 may further comprise a user interface controller 560.

The processor 510 may be, e.g., a central processing unit (CPU), a microprocessor, a digital signal processor (DSP), a graphics processing unit, or the like. FIG. 5 shows one processor 510, but the computer apparatus 160 may comprise a plurality of processors.

The memory 520 may be for example a non-volatile or a volatile memory, such as a read-only memory (ROM), a programmable read-only memory (PROM), erasable programmable read-only memory (EPROM), a random-access memory (RAM), a flash memory, a data disk, an optical storage, a magnetic storage, a smart card, or the like. The computer apparatus 160 may comprise a plurality of memories. The memory 520 may be constructed as a part of the computer apparatus 160 or it may be inserted into a slot, port, or the like of the computer apparatus 160 by a user. The memory 520 may serve the sole purpose of storing data, or it may be constructed as a part of an apparatus serving other purposes, such as processing data.

The user interface controller 560 may comprise circuitry for receiving input from a user of the computer apparatus 160, e.g., via a keyboard, graphical user interface shown on the display of the user interfaces 240 of the computer apparatus 160, speech recognition circuitry, or an accessory device, such as a headset, and for providing output to the user via, e.g., a graphical user interface or a loudspeaker.

The communication interface module 550 implements at least part of radio transmission. The communication interface module 550 may comprise, e.g., a wireless or a wired interface module. The wireless interface may comprise such as a WLAN, Bluetooth, infrared (IR), radio frequency identification (RF ID), GSM/GPRS, CDMA, WCDMA, LTE (Long Term Evolution), or 5G radio module. The wired interface may comprise such as universal serial bus (USB) or National Marine Electronics Association (NMEA) 0183/2000 standard for example. The communication interface module 550 may be integrated into the remote computer apparatus 160, or into an adapter, card or the like that may be inserted into a suitable slot or port of the remote computer apparatus 160. The communication interface module 550 may support one radio interface technology or a plurality of technologies. The computer apparatus 160 may comprise a plurality of communication interface modules 550. Sensor data items from engines 125, 170-172, 291 and/or oil lubrication data may be downloaded from the server apparatus 130 and stored to the remote computer apparatus 160.

A skilled person appreciates that in addition to the elements shown in FIG. 5, the computer apparatus 160 may comprise other elements, such as microphones, extra displays, as well as additional circuitry such as input/output (I/O) circuitry, memory chips, application-specific integrated circuits (ASIC), processing circuitry for specific purposes such as source coding/decoding circuitry, channel coding/decoding circuitry, ciphering/deciphering circuitry, and the like. Additionally, the computer apparatus 160 may comprise a disposable or rechargeable battery (not shown) for powering when external power if external power supply is not available.

Figure 6:
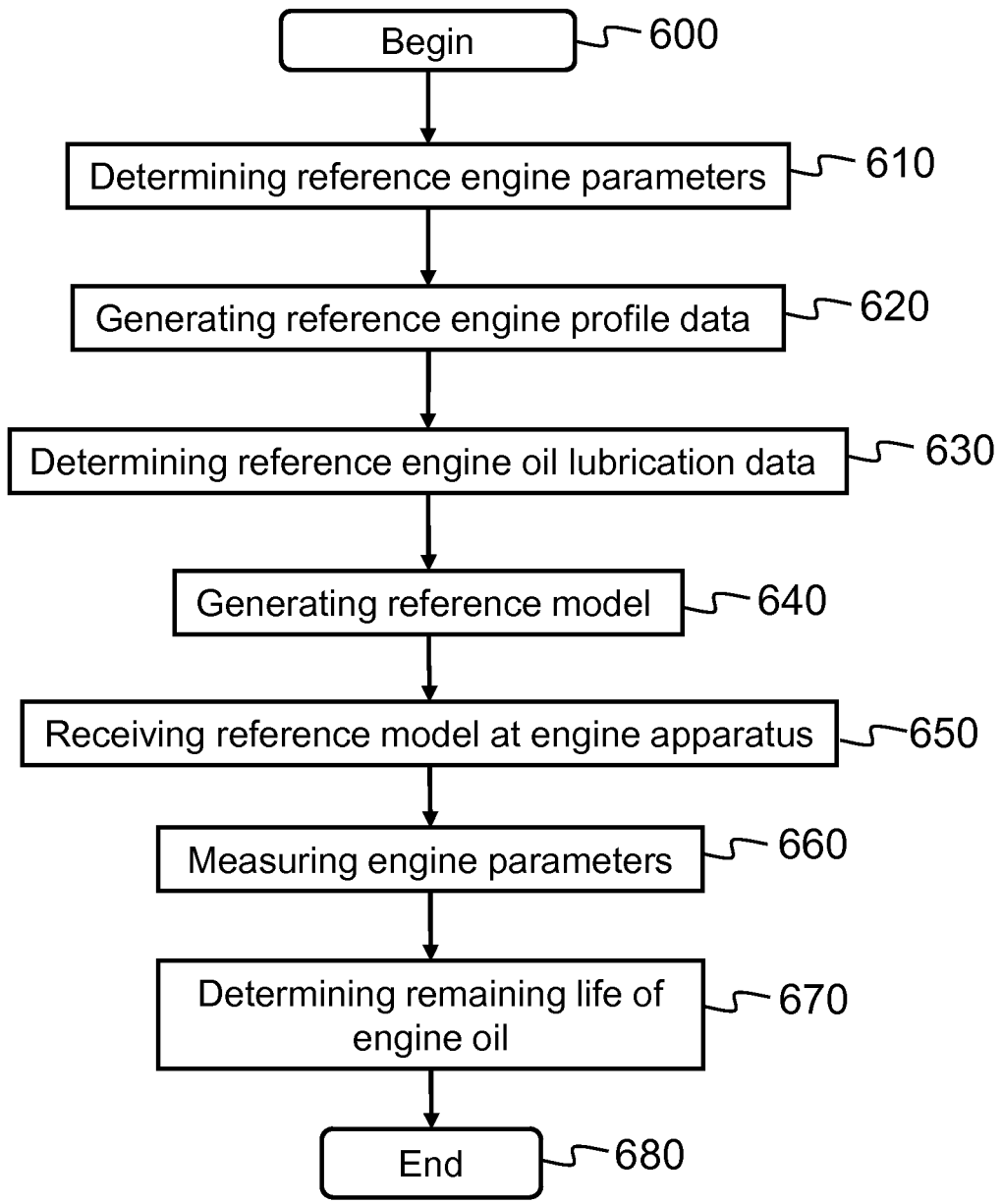
FIG. 6 shows a flow diagram showing operations in accordance with an example embodiment of the invention.

FIG. 6 shows a flow diagram showing operations in accordance with an example embodiment of the invention. In step 600, the method for determining remaining life of engine oil in an engine is started. In step 610, reference engine parameters of a reference engine are determined. In step 620, reference engine profile data is generated based on the reference engine parameters. In step 630, reference engine oil lubrication data is determined based on mechanical testing of an oil sample from the reference engine. In step 640, a reference model is generated by associating the reference engine profile data with the reference engine oil lubrication data. In step 650, the reference model is received at an engine apparatus. In step 660, engine parameters of an engine of the engine apparatus are measured. In step 670, remaining life of engine oil in the engine of the engine apparatus is determined using the reference model and the engine parameters. The method is ended in step 680.

Figure 7:
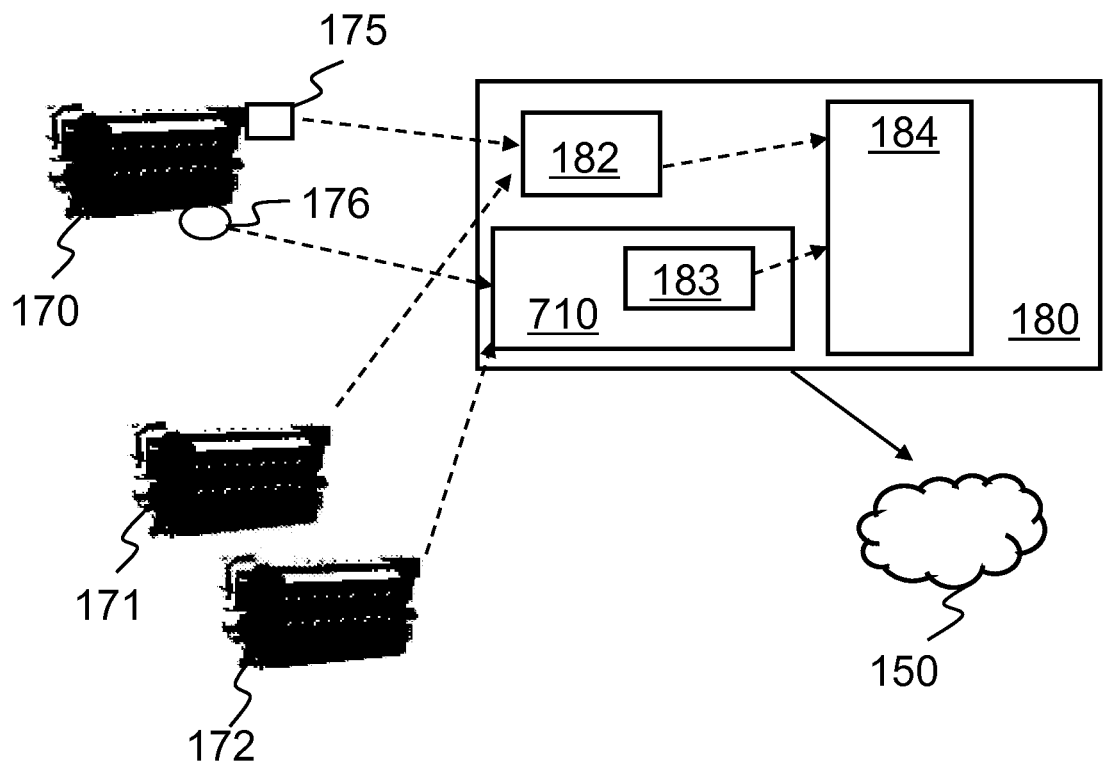
FIG. 7 shows a schematic diagram of an exemplary engine apparatus related items for determining remaining life of engine oil in accordance with an example embodiment.

FIG. 7 shows a schematic diagram 700 of an exemplary engine apparatus related items for determining remaining life of engine oil in accordance with an example embodiment.

First, from a plurality of candidate reference engines 170-172 at least one reference engine 170 and related engine and oil data is selected.

In an embodiment, selection information may be received for a plurality of reference engines from an operator of the system or defined automatically based on engine type identifiers, for example. The reference engine profile data may be generated by determining reference engine parameters of the plurality of reference engines based on the selection information.

At least one reference engine 170-172 is configured to generate the reference engine profile data 182 by determining reference engine parameters 175 of the reference engine 170-172. The reference engine parameters 175 may be detected using at least one sensor either integrated to the engine 170 or external to the engine 170. The reference engine profile data 182 may be generated based on the reference engine parameters (sensor data) 175 from at least one engine 170. The reference engine parameters may relate to different operation conditions of the reference engine.

At least one reference engine 170-172 is configured to generate reference engine oil lubrication data 183 by mechanical testing of an oil sample 176 from the reference engine 170-172. The mechanical testing of the oil sample 176 may be done by a friction test rig 710 or any test device 710 configured to perform mechanical tribological lubricity test of the oil sample 176. The test device 710 may be a separate test device and not integrated to the same device as other elements of apparatus 180.

Reference engine 170-172 related measurements, data collection and transceiving may be carried out by a reference engine data apparatus 180. A reference model 184 is generated by associating the reference engine profile data 182 with the reference engine oil lubrication data 183. The reference engine oil lubrication data 183 is thus resulting from oil lubricity data (Stribeck type friction data, for example).

Collected data 182,183 may be processed based on, combining engine data 182 to lubricity performance data 183 of lube oil 176 into an independent mathematical function, for example. This function will not require look-up tables or polynomial fitting of sample or sensor data.

In an embodiment, the collected data of reference engine profile data 182 and the reference engine oil lubrication data 183 may be processed at reference engine data apparatus 180 or transmitted to the server apparatus 130 over network 150 for processing.

In an embodiment, the reference model 184 may be transmitted to a server apparatus 130, 131 for storing and processing over connection 181. The reference engine profile data 182 and/or the reference engine oil lubrication data 183 may also be transmitted over network 150 to a server apparatus 130, 131 for storing and processing. The reference model 184 may also be generated at the server apparatus 130, 131.

In an embodiment, reference model data of the reference model may be maintained at a server apparatus, and dynamically updating the reference model data over network 150 in response to receiving reference engine profile data 182 or reference engine oil lubrication data 183.

In an embodiment, the reference engine parameters 175 and oil samples 176 may be received and processed at engine manufacturer when testing the engines in test lab and before sending the engine(s) 170-172 to customers. The reference engines(s) 170-172 may also be test engines (not sent to customers) that are run at test lab with various operating profiles and various environmental effects to gather reference data for reference model calculation.

Figure 8:
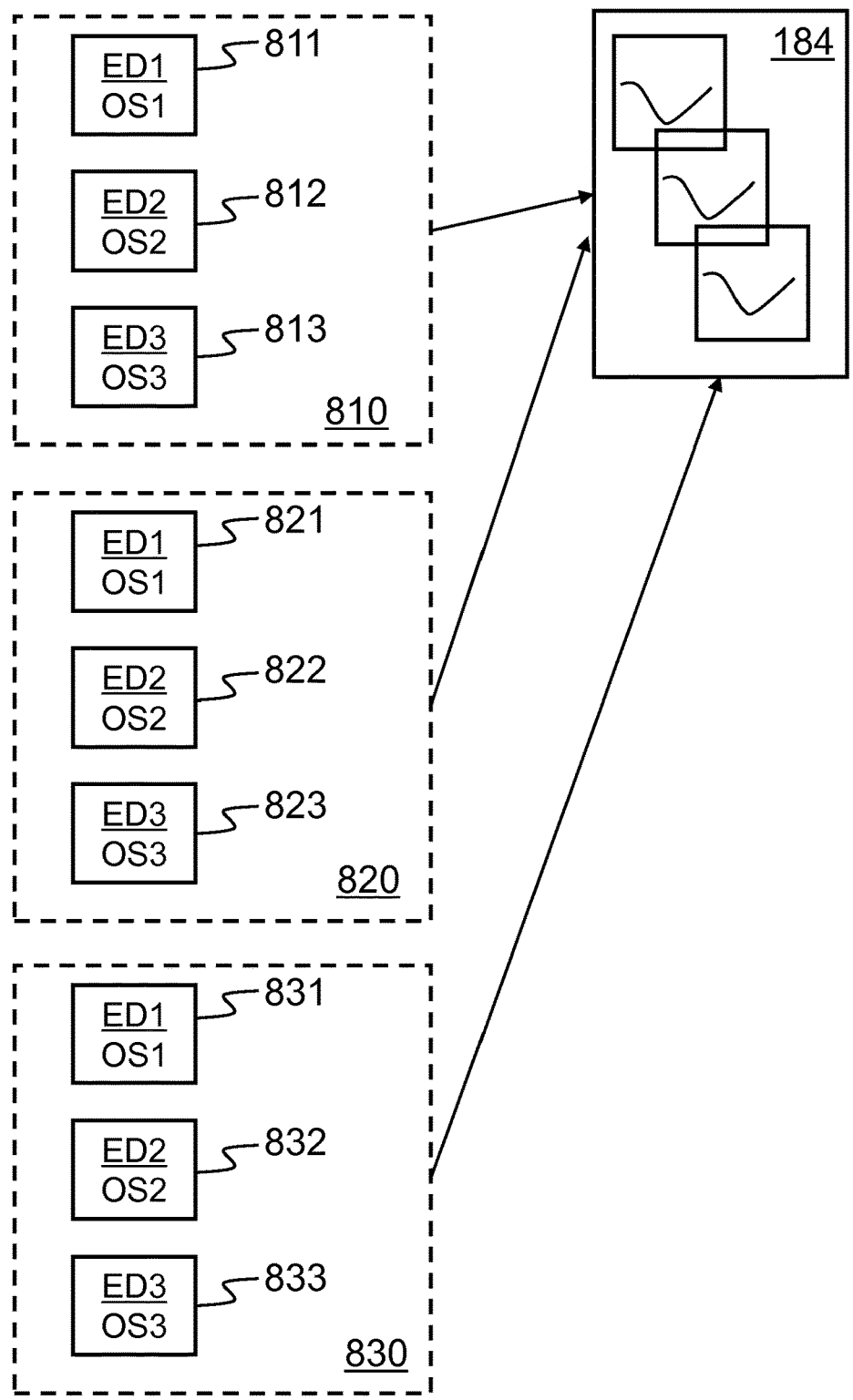
FIG. 8 shows a schematic diagram of an exemplary engine apparatus related items for generating a reference model by associating the reference engine profile data with the reference engine oil lubrication data in accordance with an example embodiment.

FIG. 8 shows a schematic diagram 800 of an exemplary engine apparatus related items for generating a reference model by associating the reference engine profile data with the reference engine oil lubrication data in accordance with an example embodiment.

In an embodiment, at least one of a server apparatus (such as server 130 in FIG. 1) and a reference engine data apparatus 180 is configured to perform a computer implemented method for generating a reference model by associating the reference engine profile data with the reference engine oil lubrication data. A plurality of reference engine data items 810-830 may be received.

Engine data item 810 may comprise any data set 811-813 from the first reference engine, for example. The engine data item 810 may comprise a first data set 811 of reference engine profile data (ED1, data 182 in FIG. 1) with the reference engine oil lubrication data (OS1, data 183 in FIG. 1) defined based on the oil sample reflecting operation of the engine in view of the reference engine profile data (ED1). Corresponding data sets 812-813 may be determined based on different engine profile data (ED2-3) with the reference engine oil lubrication data (OS2-3) defined based on the oil sample reflecting operation of the engine in view of the reference engine profile data (ED2-3), respectively.

Further engine data items 820-830 may comprise any data set 821-833 from the second and third reference engine, or any other reference engine, accordingly.

A reference model 184 is generated by associating the reference engine profile data with the reference engine oil lubrication data, wherein a plurality of different reference engine profile data and the reference engine oil lubrication data 811-813 from the single engine data item 810 may be used. In some embodiments, a plurality of different engine data items 810-830 may be used for a single model 184.

In an embodiment, the reference model 184 may be configured to comprise a dynamic model associating different engine profile data with respective oil lubrication data. Such model can then be used at operating engine to estimate current status of the engine oil and predict its future performance in view of the operating profile.

Figure 9:
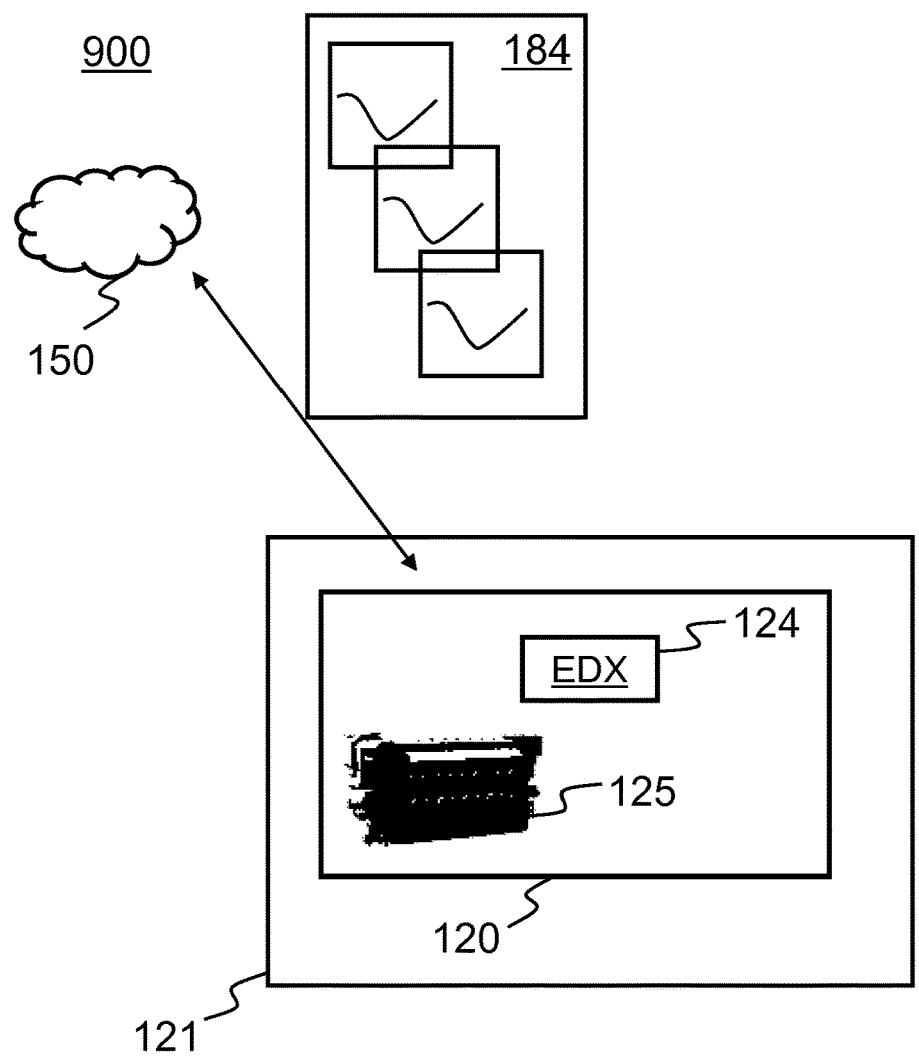
FIG. 9 shows a schematic diagram of an exemplary engine apparatus related items for determining remaining life of engine oil in an engine, in accordance with an example embodiment.

FIG. 9 shows a schematic diagram 900 of an exemplary engine apparatus related items for determining remaining life of engine oil in an engine 125, in accordance with an example embodiment.

In an embodiment, the reference model 184 is received at an engine apparatus 120 of a marine vessel 121 or a power plant 121, for example, over the network 150 or installed locally as a service function. Engine parameters 124 relating to operation conditions of an engine 125 of the engine apparatus 120 may be measured and used for processing but alternatively only the model 184 may be used. Remaining life of engine oil in the engine 125 of the engine apparatus 120 may be determined using the reference model 184 and the engine parameters (EDX) 124, or only using the reference model 184.

In an embodiment, an engine 125 or an engine apparatus 120 is identified based on identification information, and the (engine/apparatus) identification information may be transmitted to the server apparatus over network 150. At the server apparatus, the reference model may be generated by associating reference engine profile data with reference engine oil lubrication data based on the (engine/apparatus) identification information and after that the generated reference model 184 may be received at the engine apparatus 120.

In an embodiment, remaining life of the engine 125 lubricant oil may be determined using the function of the reference model 184. Furthermore, current performance characteristics of the engine 125 oil may be determined using the function of the reference model 184. In addition, predicted future performance characteristics of the engine 125 oil may be determined using the function of the reference model 184. The engine 125 may be a marine vessel engine or a power plant engine, for example.

Lubricated sliding contacts in combustion engines are designed to operate in a certain lubrication regime to optimize wear and friction. However, as the lube oil deteriorates this lubrication regime shifts and the engine component could operate in a different regime.

In an embodiment, the function of the reference model 184 is configured to predict this behavior and calculate the lubrication performance and wear of components of the engine 125 and predict the operating profile of the engine 125 to estimate component life.

Lube oil samples may be obtained from reference engines with known operation condition and evaluated in terms of lubricity based on tribological mechanical testing.

Data acquired through testing and analyses of the oil samples may be numerically investigated (e.g. measured friction, speed load or such).

The experimental reference data gained may be used to create the trained model 184.

The model 184 is configured together with the on-site engine data 124 (e.g. load, speed, start stop, ramp up time) to identify the current and predict the future component performance and wear regime. The model 184 is configured to generate information on e.g. optimizing the engine performance to minimize wear and prolong critical component lifetime or predict component life, for example.

Figure 10:
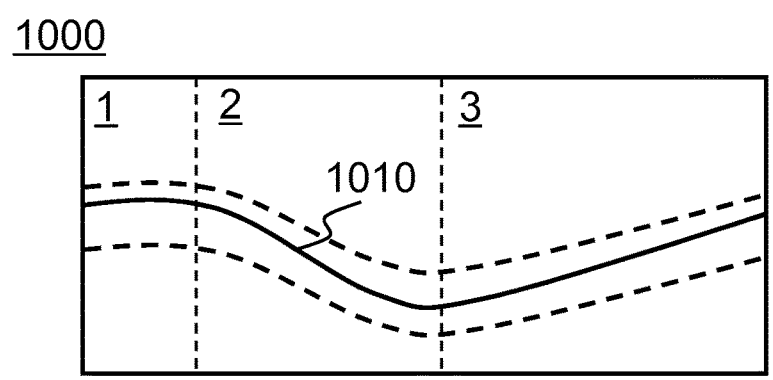
FIG. 10 shows a schematic diagram of an exemplary dynamic function for determining remaining life of engine oil in an engine, in accordance with an example embodiment.

FIG. 10 shows a schematic diagram 1000 of an exemplary dynamic function for determining remaining life of engine oil in an engine 125, in accordance with an example embodiment.

In an embodiment, the engine apparatus 120 may generate a dynamic function 1010 using the reference model 184 and the engine parameters 124. The dynamic function 1010 may be a dynamic Stribeck curve generated based on the reference model 184 and any available local engine apparatus parameters 124, for example.

A Stribeck curve is a fundamental concept in the field of tribology. It shows that friction (y-axis) in fluid-lubricated contacts is a non-linear function of the contact load, the lubricant viscosity and the lubricant entrainment speed (x-axis). For a contact of two fluid-lubricated surfaces, the Stribeck curve shows the relationship between the so-called Hersey number, a dimensionless lubrication parameter, and the friction coefficient. The Hersey number is defined as:

Hersey number=$(\eta \cdot N)/P$ where $\eta$ is the dynamic viscosity of the fluid, N is the entrainment speed of the fluid and P is the normal load in the tribological contact. Thus, for a given viscosity and load, the Stribeck curve shows how friction changes with increasing velocity. Based on the typical progression of the Stribeck curve, three lubrication regimes can be identified.

First regime 1 in FIG. 10 is called Boundary lubrication, wherein solid surfaces come into direct contact, and load is supported mainly by surface asperities, and high friction exists.

Second regime 2 in FIG. 10 is called Mixed lubrication, wherein some asperity contact exists, and load is supported by both asperities and the liquid lubricant.

Third regime 3 in FIG. 10 is called Hydrodynamic lubrication, wherein negligible asperity contact exists, and load is supported mainly by hydrodynamic pressure.

The engine apparatus 120 is configured to dynamically adjust the function 1010 to determine the lubricity performance of the engine oil without taking any samples on-site. The function 1010 may be generated by determining reference engine oil lubrication data based on mechanical testing of an oil sample from the reference engine and generating the reference model with function 1010 by associating the reference engine profile data with the reference engine oil lubrication data. Using the dynamic function 1010, the engine apparatus 120 may be configured to estimate the current and future performance of the current lube oil, based on the information of its real operating condition and its predicted operating profile.

When knowing the dynamic function 1010, the engine apparatus 120 may be configured to estimate the optimum time for oil change.

In an embodiment, the engine apparatus 120 is configured to measure engine parameters relating to operation conditions of the engine 125 of the engine apparatus 120 and to determine based on the dynamic function 1010 the remaining life of engine oil in the engine 125 of the engine apparatus 120 using the dynamic function 1010 and the engine parameters 124. Based on the dynamic function 1010, the engine apparatus 120 may estimate on which regime the engine 125 will be operated and when is the optimum time for oil change, accordingly.

Figure 11:
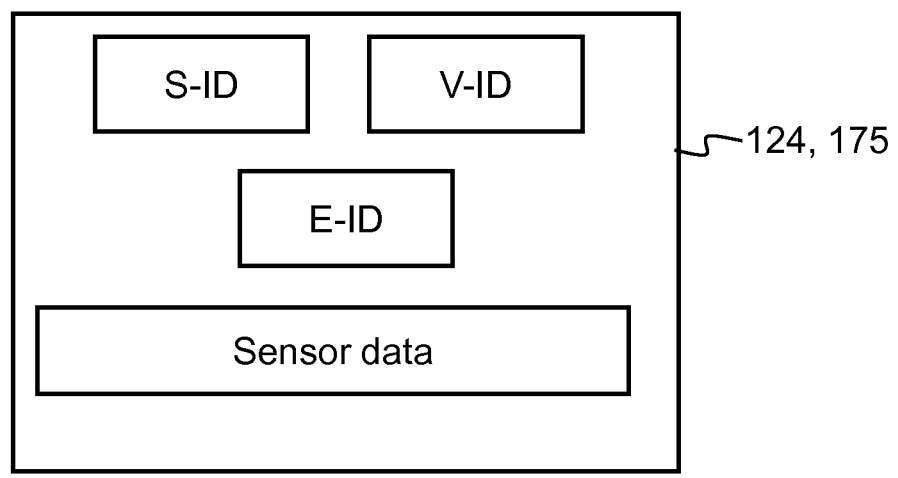
FIG. 11 shows a schematic diagram of a sensor data item in accordance with an example embodiment.

FIG. 11 shows a schematic diagram of a sensor data item in accordance with an example embodiment. The sensor data item 124, 175 as disclosed may comprise at least one identifier.

In an embodiment, the engine 291 and at least one sensor device 290 (see e.g. FIG. 2) are configured to generate sensor data items based on the received identification system data and sensor data. The sensor data item may thus comprise sensor data generated by the sensor device 290 and an identifier information. The identifier information may comprise at least one of the following: sensor-ID (S-ID); engine-ID (E-ID), and vessel-ID (V-ID) that may comprise at least part of the received automatic identification system data, for example.

A sensor data item, such as engine parameters 124, is generated by a sensor device of the marine vessel 121 or power plant and transmitted to the server apparatus 130. Sensor data items may be processed at the engine apparatus 120 before transmitting or they may be sent without further processing to the server 130.

Without in any way limiting the scope, interpretation, or application of the claims appearing below, a technical effect of one or more of the example embodiments disclosed herein is an improved system for an engine apparatus.

A technical effect of one or more of the example embodiments disclosed herein is that accuracy of oil life-time estimation is improved. A technical effect of one or more of the example embodiments disclosed herein is that fuel efficiency of an engine is improved. A further technical effect of one or more of the example embodiments disclosed herein is that operational efficiency of an engine apparatus, is improved. Another technical effect of one or more of the example embodiments disclosed herein is that oil lubrication properties may be accurately defined without taking an oil sample at on-site engine apparatus.

Although various aspects of the disclosed embodiments are set out in the independent claims, other aspects of the disclosed embodiment comprise other combinations of features from the described embodiments and/or the dependent claims with the features of the independent claims, and not solely the combinations explicitly set out in the claims.

It is also noted herein that while the foregoing describes example embodiments of the present disclosure, these descriptions should not be viewed in a limiting sense. Rather, there are several variations and modifications that may be made without departing from the scope of the present disclosure as defined in the appended claims.

The invention claimed is:

1. A computer implemented method for determining remaining life of engine oil in an engine, the method comprising:

determining reference engine parameters of a reference engine;

generating reference engine profile data based on the reference engine parameters;

determining reference engine oil lubrication data based on mechanical testing of an oil sample from the reference engine, wherein the mechanical testing of the oil sample comprises tribological lubricity test of the oil sample and the tribological lubricity test is configured to be evaluated based on friction test rig results;

generating a reference model by associating the reference engine profile data with the reference engine oil lubrication data;
receiving the reference model at an engine apparatus;
measuring engine parameters of an engine of the engine apparatus; and
determining remaining life of engine oil in the engine of the engine apparatus using the reference model and the engine parameters.

2. The method of claim 1, further comprising:
receiving selection information for a plurality of reference engines; and
generating the reference engine profile data by determining reference engine parameters of the plurality of reference engines based on the selection information.

3. The method of claim 1, further comprising:
determining the reference engine parameters based on sensor data received from at least one reference engine.

4. The method of claim 3, wherein the reference engine parameters relate to different operational conditions of the reference engine.

5. The method of claim 3, wherein the reference engine parameters relate to operational and environmental measurement data of the reference engine.

6. The method of claim 5, wherein the operational measurement data comprises at least one of the following:
number of engine starts;
operating hours since last oil change;
load cycles of the engine;
miles traveled with the engine;
amount of fuel used by the engine; and
sensor data of the engine.

7. The method of claim 2, further comprising:
determining the reference engine oil lubrication data based on mechanical testing of oil samples from the plurality of reference engines based on the selection information.

8. The method of claim 1, further comprising:
determining the reference engine oil lubrication data based on the tribological lubricity test of the oil sample, wherein the reference engine oil lubrication data comprises Stribeck type of friction data.

9. The method of claim 1, further comprising:
maintaining reference model data of the reference model at a server apparatus; and
dynamically updating the reference model data in response to receiving reference engine profile data or reference engine oil lubrication data.

10. The method of claim 9, further comprising:
transmitting engine apparatus identification information to the server apparatus;
generating the reference model by associating reference engine profile data with reference engine oil lubrication data based on the engine apparatus identification information; and
receiving the generated reference model at an engine apparatus.

11. The method of claim 1, wherein the engine parameters relate to operational or environmental measurement data of the engine.

12. The method of claim 1, further comprising:
associating the reference engine profile data with the reference engine oil lubrication data by combining to generate a function of the reference model.

13. The method of claim 12, further comprising:
determining remaining life of the engine oil using the function of the reference model.

14. The method of claim 12, further comprising:
determining current performance characteristics of the engine oil using the function of the reference model.

15. The method of claim 12, further comprising:
determining predicted future performance characteristics of the engine oil using the function of the reference model.

16. The method of claim 1, wherein the reference model is received and the remaining life of engine oil in the engine of the engine apparatus is determined at the engine apparatus.

17. An engine apparatus, comprising:
an engine;
a communication interface;
at least one processor; and
at least one memory including computer program code;
the at least one memory and the computer program code configured to, with the at least one processor, cause the apparatus to:
receive a reference model, the reference model being configured to be generated by associating reference engine profile data with reference engine oil lubrication properties, wherein the reference engine profile data is configured to be generated by determining reference engine parameters relating to a different operation conditions of the reference engine, and the reference engine oil lubrication properties are configured to be determined for the different operation conditions based on mechanical testing of an oil sample from the reference engine, wherein the mechanical testing of the oil sample comprises tribological lubricity test of the oil sample and the tribological lubricity test is configured to be evaluated based on friction test rig results;
measure engine parameters relating to operation conditions of the engine of the engine apparatus; and
determine remaining life of engine oil in the engine of the engine apparatus using the reference model and the engine parameters.

18. The engine apparatus of claim 17, wherein the reference engine oil lubrication data comprises Stribeck type of friction data.

19. A server apparatus comprising:
a communication interface;
at least one processor; and
at least one memory including computer program code;
the at least one memory and the computer program code configured to, with the at least one processor, cause the apparatus to:
generate a reference model by associating the reference engine profile data with the reference engine oil lubrication data, wherein the reference engine profile data is generated by determining reference engine parameters of a reference engine and the reference engine oil lubrication data is determined based on mechanical testing of an oil sample from the reference engine, wherein the mechanical testing of the oil sample comprises tribological lubricity test of the oil sample and the tribological lubricity test is configured to be evaluated based on friction test rig results; and
transmit the reference model to an engine apparatus for measuring engine parameters relating to operation conditions of an engine of the engine apparatus, and for determining remaining life of engine oil in the engine of the engine apparatus using the reference model and the engine parameters.

20. The server apparatus of claim 19, wherein the reference engine oil lubrication data comprises Stribeck type of friction data.

\* \* \* \* \*